United States Patent [19]

Sharma

[11] 4,360,358

[45] Nov. 23, 1982

[54] IMMUNOASSAY WITH SOLID PHASE HAVING COATING CONTAINING BLOOD PLATELET SUBSTITUTE

[76] Inventor: Yash Sharma, 2766 January Cts., Falls Church, Va. 22043

[21] Appl. No.: 127,989

[22] Filed: Mar. 7, 1980

[51] Int. Cl.³ ...................... G01N 33/54; G01N 33/56
[52] U.S. Cl. .................................. 23/230 B; 23/915; 422/61; 424/1; 424/12; 427/2; 435/7
[58] Field of Search .................... 23/230 B; 424/12, 1; 427/2; 422/61

[56] References Cited

U.S. PATENT DOCUMENTS

| | | | |
|---|---|---|---|
| 3,395,210 | 7/1968 | Lenahan | 23/230 B |
| 3,880,714 | 4/1975 | Babson | 435/13 |
| 4,069,352 | 1/1978 | Parsons | 427/2 |
| 4,254,096 | 3/1981 | Monthony | 23/230 B X |
| 4,256,724 | 3/1981 | Rutner | 23/230 B X |
| 4,264,571 | 4/1981 | Goldstein | 23/230 B X |
| 4,278,651 | 7/1981 | Hales | 23/230 B X |

OTHER PUBLICATIONS

Chemical Abstracts, 90: 18764v (1979).

*Primary Examiner*—Sidney Marantz
*Attorney, Agent, or Firm*—Bacon & Thomas

[57] ABSTRACT

A method for preparing an immunologically active coated solid phase, suitably in the form of a coated tube or a polymer latex, for solid phase immuno assays, in particular radio immuno assays, is disclosed. The method comprises coating a solid support which has an organic polymer surface with a coating solution containing the immunologically active agent, e.g., an antibody or antigen, a hydroxy lower alkyl amine, preferably tris(hydroxymethyl) amino methane, and a platelet substitute. The solid support can be a solid organic polymer, such as polystyrene, which can be coated directly with this coating solution. If the immunologically active agent has a molecular weight of below 20000, the organic polymer surface of the solid phase is a matrix of a gel forming hydrophilic polymer. In this case the platelet substitute and the hydroxylower alkyl amine can be omitted from the coating solution.

9 Claims, No Drawings

IMMUNOASSAY WITH SOLID PHASE HAVING COATING CONTAINING BLOOD PLATELET SUBSTITUTE

BACKGROUND OF THE INVENTION

The present invention relates to an immunologically active coated solid phase for solid phase immunological assays in particular for solid phase radioimmuno assay techniques, to methods for preparing immunologically active solid phase and to immunological test methods and kits using same.

It is well known in the medical art that a variety of chemical substances, either as such or in form of a complex with a body protein, have antigenic activity, that is they are capable of acting as an antigen; i.e., when introduced into animals they are capable of eliciting an immune response and causing the formation of a specific antibody or immunological binder.

In the following specification and claims the term "antigen" designates all substances which, as such, or in form of a protein-complex, have antigenic activity. Antigens include high molecular substances such as proteins and other polypeptides and polysaccharides, for example many proteinaceous components of human body liquids, hormones, bacteria-produced toxins, virus, etc., lower molecular weight chemicals including many drugs which are so-called haptens, that is they react with a body protein to form a protein-complex with antigenic activity, as well as lower weight substances, which as such are capable of antigenic activity.

Antibodies are proteins which exhibit a specific immunological activity against the antigen which caused their formation. Antibodies have a molecular weight in the range of 150,000 and are very similar in their overall protein-structure, but are distinguished from each other by their specific affinity to different antigens.

Certain low molecular weight antigens are not capable of causing formation of an antibody, but elicit the formation of a lower molecular weight peptide, e.g. a peptide having a molecular weight in the range of between about 5,000 and 120,000 which possesses an antibody-like specific immunological activity against the antigen which caused their formation, that is, they are capable of selectively binding these antigens in an immunological reaction. These peptides are known as immunological binders.

Immunological methods for inducing antibody formation or formation of an immunological binder in animals and recovering the antibody or immunological binder from the animal, e.g., in form of an antiserum are well known in the art.

In the following specification and claims, the term "antibody" is meant to denote a proteinaceous material which exhibits antibody activity, that is, the antibody in substantially pure form or in form of a mixture having a high antibody-activity, e.g., an antiserum. The term "immunologically active binder" is meant to denote a peptide material which exhibits antibody-like immunological binding activity, that is, the peptide is substantially pure form or in form of mixture having a high antibody-like binding activity, e.g., an antiserum.

In the following specification and claims, the term "immunologically active agent" is meant to include antigens, antibodies and immunologically active binders.

Immunological diagnostic test methods generally comprise reacting a liquid in which a given antigen is to be determined with a reagent containing a known amount of an antibody or immunological binder, or reacting a reagent containing a known amount of antigen with a liquid wherein an antibody or immunological binder is to be determined, separating the antigen/antibody or antigen/immunological binder complex from the unreacted components and determining the residual amount of unreacted antigen or antibody, or the amount of reacted antigen or antibody in the complex reaction product.

Different methods which are known in the art can be used for the determination including microscopic and electromicroscopic examination, fluorescent method wherein a dyestuff is used to make the antigen or the antibody visible and radioimmuno assay (in the following, abbreviated as "RIA") techniques.

In radioimmunological methods, a known amount of e.g. an antigen, which is labeled with a radioactive isotope, is added to the liquid, the antigen of which is to be determined. The amounts of labeled and unlabeled antigen which react with the antibody are in proportion to their relative concentrations in the test liquid. The radioactivity of the antigen/antibody reaction product or of the unreacted residual antigen is measured.

For calculation of the antigen content of the original test liquid, the measured amount of radioactivity is compared with a standard curve which is prepared by reacting the same antibody reagent with standard samples containing known amounts of labeled and unlabeled antigen.

For any quantitative immunological test procedures, it is mandatory that the content of immunologically active agent in the reagent which is used in a test series is the same throughout the test series, and that quantitative separation between the complex reaction product and unreacted material can be achieved.

For facilitating the separation of the complex reaction product from the reaction mixture, solid phase immuno assay techniques have been developed for immunological tests involving antigen/antibody reactions. In these solid phase immuno assays, the antibody-containing reagent is a solid organic polymer substrate onto the surface of which the antibody is bonded.

Polymeric organic materials possess a certain adsorption capacity for adsorbing proteinaceous substances on their surfaces. The degree of adsorption and affinity of the polymer towards the adsorbed substance is dependent on the molecular weight of the adsorbed substance and decreases with decreasing molecular weight of the latter.

The technique of solid phase RIA was introduced by Catt and coworkers. The bonded antibody, e.g., an antiserum, will selectively react with, and bind antigen for which it is specific. When radioactively labeled antigen is added to the sample to be assayed, such as blood serum, urine, etc., labeled and unlabeled antigen will be bound in proportion to their concentration in the test sample. Thus, by incubating the antibody containing solid phase with the test sample, and then counting the radiation content of, e.g., the solid phase, the original concentration of unlabeled antigen therein can be determined.

Of course, the amount of antigen which is bonded to the solid phase during the assay will depend on the amount of antibody which is present on the surface of the solid phase. Therefore, the accuracy of solid phase immuno assays, in particular, solid phase radioimmuno assays and thus their practical usefulness, will depend on the availability of a method by means of which uniform and reproducible antibody-coated solid phases can be prepared.

Catt and coworkers have reported solid phase RIA techniques wherein the polymer of the solid phase is in form of powder (Biochem. J. 100:31 c (1966), plastic tubes (Science, 158:1570 (1967)) and plastic discs (J. Lab. and Clin. Med. 70:820 (1967)). In all cases the solid coated phase is maintained in a wet state and is freshly prepared or stored in a solution of bovine serum albumin. In U.S. Pat. No. 3,646,346, Catt discloses the use of an antibody coated test tube of polymeric material capable of adsorbing antibodies in RIA. The inside of the test tube is contacted with a buffered aqueous solution of the antibody, e.g. antiserum, for several hours, then the liquid is aspirated and the test tube is washed with saline. This coating procedure has serious disadvantages in that the resulting coating is not uniform, the attachment of the antibodies to the polymer surface is very poor, the concentration of antibody on the polymer surface is insufficiently low and inconsistent, and the coating is not sufficiently stable for routine laboratory handling.

Garrison et al (U.S. Pat. No. 3,790,663) discloses a similar method for binding antiserum to the surface of a plastic polymer, e.g., to the inside wells of a plastic microlitration tray. The wells are filled with antiserum which is diluted with a sodium borate buffer solution after one hour the antiserum is aspirated, the wells are rinsed and allowed to dry. The resulting coating has the same disadvantages as are mentioned above.

Crook et al. (U.S. Pat. No. 3,619,371) discloses a polymer matrix having biochemically active substances chemically bonded thereto. Into a polymer molecule triazinyl linking groups are chemically introduced and the triazinyl substituted polymer is then reacted with the biochemically active substance, e.g., an enzyme, antigen or antibody.

SUMMARY OF THE INVENTION

It is an object of the present invention to provide a coating method for preparing an immunologically active coated solid phase, in particular a coated tube, for immuno assays, in particular, solid phase RIA techniques, which overcomes the drawbacks of the prior art coating methods and yields coatings of consistent high quality and reproducibility.

It is a further object of the present invention to provide a coating method which is applicable not only to antibodies, but also to lower molecular weight immunologically active agents.

It is a further object of the present invention to provide such a coating method which yields coatings of a high degree of uniformity and yields coated solid phase materials, in particular, coated tubes, wherein a sufficiently strong attachment of the immunologically active agent to the surface of the solid phase, e.g., the inner surface of a test tube, is achieved to allow easy handling in everyday clinical laboratory procedures.

It is a further especial object of the present invention to provide a method by means of which a large number of individual support material units, e.g., test tubes, can be provided with a coating of identical quality and identical immunological activity, and thus, a simple means for accurate large scale clinical screening can be prepared.

It is a further object to provide such a coating method by means of which a high immunological binding activity and sensitivity of the immunologically active agent in the immunologically active coating is achieved and the loss of the expensive immunologically active agent is held at a minimum.

It is a further object to provide such a coating method by means of which a coated immunologically active solid phase, e.g., a coated test tube, of excellent storage stability can be obtained.

It is a further object of the present invention to provide a storage-stable diagnostic kit for solid phase immuno assays.

In order to accomplish the foregoing objects according to the present invention, there is provided a method for preparing an immunologically active coated solid phase by coating the surface of a solid support material having an organic polymer surface with an immunologically active agent which comprises the steps of (a) contacting the organic polymer surface of the solid support material with an aqueous coating solution havinge a pH value of from about 8.5 to about 10.5, and comprising dissolved therein, an amount of from about 0.035 to about 0.05 mol/l of a water soluble protein-compatible primary or secondary hydroxy lower alkyl amine, an amount of between 0.05 and about 20 g/l of a water soluble immunologically active agent, and an amount of from about 0.5 to about 10 g/l of a blood platelet substitute for a sufficient period of time to allow an immunologically effective amount of the immunologically active agent to be attached to the organic polymer surface of the solid support material to obtain an immunologically active coating thereon, (b) removing the coating solution from the coated solid support material, (c) allowing the coated solid support material to dry.

Depending on the molecular weight and the sensitivity of the immunologically active agent to be coated, the solid support material may be an organic water insoluble polymer, the surface of which is treated with the coating solution, or the organic polymer surface of the support material is a water-wettable matrix of a hydrophyllic gel-forming organic polymer. In the latter case, the platelet substitute and/or the lower hydroxyalkylamine may be omitted from the coating solution.

Furthermore, according to the present invention, there are further provided methods and diagnostic test kits for carrying out solid phase immuno assays using the immunologically active solid phase according to the present invention.

DETAILED DESCRIPTION OF THE INVENTION

The coating method according to the present invention is applicable for preparing a wide variety of immunologically active solid phase for solid phase immuno assay techniques, in particular, RIA techniques.

By means of this method, an outstandingly strong attachment of the immunologically active agent on the organic polymer surface of the solid support and uniform and reproducible coatings are achieved with a large variety of different immunologically active agents, thus making solid phase immuno assay techniques available for a large field of clinical testing.

Immuno assays, including RIA techniques for which an immunologically active solid phase can be prepared by the instant coating method are useful for a variety of diagnostic procedures, e.g., for detecting and determining naturally occuring components in human body liquids, e.g., hormones and the like, abnormally high or low concentrations of which can serve as an accurate indication of especial conditions (e.g. pregnancy) or various diseases and deficiencies in the human body and/or for monitoring the course of a disease under therapeutic treatment, for detecting or determining the level of alien components in human body liquids, including bacterial toxins, viruses and the like, or allergens or drugs which in the form of haptans in a protein complex or as such are capable of an immunological reaction.

Immunologically active agents which can be coated in sufficient amounts onto a polymer surface to yield an active solid phase include not only antibodies, but also other immunologically active proteinaceous agents which exhibit a lower molecular weight,[1] e.g., as low as about 5,000.

[1] molecular weight determination by ultracentrifugation and calculated by method of Szedberg All antibodies are proteins of very similar overall molecular structure, having a molecular weight in the range of 150,000 which are distinguished from each other only by the specific antigen-binding sites which are reactive towards the specific antigen which causes formation of the antibody. All antibodies can readily be coated onto the surface of a solid polymer substrate by the present coating method. Examples of antibodies to which the present coating method can be applied are antibodies against hormones such as human chorionic gonadotropin (HCG) antiserum, thyroid stimulating hormone (TSH) antiserum, human growth hormone (HGH) antiserum, insulin antiserum, human placental lactogen (HPL) antiserum, luteinizing hormone (LH) antiserum, follicle stimulating hormone (FHS) antiserum, antibodies against steroids such as oestriol antiserum, cortisol antiserum, antibodies against drugs including cardiac glycosides and antibiotics, such as digoxin antiserum gentamycin antiserum, toubramycin antiserum, thyroxin (T4) antiserum, antibodies against bacterial toxins and viruses such as tetanus antiserum and other antitoxins, anti hepatitis antiserum, and the like.

Other immunologically active agents which can be coated onto the polymer surface of a solid substrate include proteinaceous materials having a molecular weight of at least 20,000 and other antigens or immunological binders having a molecular weight of at least 5,000. Examples of these groups of immunologically active agents include hormones, e.g., thyroid hormones containing 3-iodothyronine or thyroxin as a prosthetic group, haptan-protein complex of drugs and allergens, the above-mentioned hormones, e.g., HCG, HGH, AC, HPL, LH, FHS, TSH, and the like, immunological binders such as intrinsic factor which is an immunological binder for vitamin B-12 or β-lactoglobulin, which is an immunological binder for folic acid and many enzymes.

The solid support onto which the immunologically active agent is coated can take the shape of tubes, powders, granulates, pellets, discs, plates and the like. Preferably, the solid phase is provided by a test tube the inside of which is coated with the immunologically active agent, and wherein the immunological test can subsequently be carried out. In case the immunologically active agent is a polypeptide, e.g., a protein having a molecular weight of at least 20,000, it can be coated according to the present invention directly onto the surface of any solid water soluble organic polymer which does not contain functional groups which will interfere with the immunological reaction. Suitable polymers include hydrocarbon polymers such as polyethylenes, polypropylene, ethylene-propylene copolymers, polybutylenes, polystyrenes, synthetic rubbers. Other suitable organic polymers include halogenated polymers such as polyvinylchloride, polyvinylidene chloride, polytetrafluoroethylene (tradename Teflon TFE); polyamides such as nylons; polyurethanes; polyesters such as polyethylene terephthalates, polyacrylates and polymethacrylates; cellulose and cellulose derivatives; as well as copolymers each containing various of the recurring units of the foregoing polymers.

According to a preferred embodiment of the present invention, the immunological agent is coated to the inner surface of a test tube made of one of the foregoing organic polymer materials.

The degree to which a proteinaceous material is adsorbed onto an organic polymer surface increases with its molecular weight. In case the immunologically active agent has a molecular weight of below 50,000 or possesses a low immunological activity, it is advisable to enhance the adsorbing activity of the polymer surface by means of a pretreatment with an aqueous solution of a water soluble dialdehyde containing 3 to 8 carbon atoms, in particular, glutaraldehyde, prior to the coating procedure. Suitably, the surface, e.g., the inside of a tube, is treated with an 0.05 to 1% v/v aqueous solution of the aldehyde for a period of between about 1 and about 5 hours at elevated temperature, e.g., a temperature between room temperature and about 75° C. Suitably, the surface then is rinsed with water and air dried at room temperature. This pretreatment provides for a binding by covalent linkages of amino groups in addition to the bonding by adsorption.

In order to provide sufficient attachment of an immunologically active agent which has a molecular weight of below 20,000, e.g., in the range of between 5,000 and about 20,000 onto the solid support material, the polymer surface thereof has to be in the form of a water wettable polymer matrix into which the immunologically active agent can penetrate. Suitably this polymer matrix is a film coating of a protein-compatible gel-forming hydrophyllic polymer on at least a portion of the surface of the solid support material, in particular, a test tube. The organic gel forming polymer is a polymer which is soluble in water in the heat to form a liquid colloid solution which solidifies into a gel at room temperature. Suitable gel forming polymers include hydrocolloids, e.g., polysaccharides, in particular agar and agar-like polysaccharides from related maritime plants. Synthetic gel-forming polymers include acrylic acid polymers (e.g., Carbopol ®), cellulose derivatives, such as methylcellulose, carboxymethylcellulose. The film of gel forming organic polymer can be coated onto solid water insoluble polymer material, e.g., the above-cited polymers, or onto a glass or ceramic support material.

According to a preferred embodiment of the invention, a portion of the inner surface of a test tube made of glass or an organic solid polymer is coated with the film of gel forming polymer.

Suitably the matrix of gel forming polymer is applied to the surface of the solid support material by it with an aqueous colloid solution containing from about 0.5 to about 2.0%. Preferably about 1%, of the gel forming polymer, preferably agar, and having a pH value of between about 7 and about 10.

Suitably the gel forming polymer is dissolved in water in the heat, e.g., at boiling temperature to yield a clear solution on which then is allowed to cool to between about 30° and about 50° C. If necessary, the pH is adjusted. The surface of the solid support is covered with the warm solution, e.g., the solution is poured into a test tube. Excess solution is removed e.g. by aspiration, and the remaining film of colloid liquid is allowed to dry, suitably at room temperature. Suitably the amount of gel forming polymer which is applied to the surface is from about 0.5 to about 2 mg. per 1 cm² of surface area.

In case of a sufficiently heat stable immunologically active agent, the polymer matrix may be applied to the surface of the solid support simultaneously with the immunologically active agent in form of a simple warm solution containing the gel forming polymer and the immunologically active agent dissolved therein. In this manner, the immunologically active agent is embedded into the film of polymer matrix.

Whereas only for attaching certain low molecular weight immunologically active agents it is necessary that the polymer surfaces of the solid support is a matrix of a gel forming polymer, it is readily seen that such matrix coated solid support materials are equally operable where the immunologically active agent is a high molecular protein, e.g., an antibody.

The coating solution according to the present invention is an aqueous which comprises, in addition to the immunologically active agent, a water soluble protein-compatible primary or secondary hydroxy-lower alkyl amine and a platelet substitute or a mixture of a Hageman-factor with a platelet substitute.

The pH value of the coating solution is adjusted to from about 8.5 to about 10.5, preferably to from about 9.0 to about 10.0, most preferably to from about 9.2 to about 9.6.

It is advisable that the coating solution is substantially free of metallic cations with the exception of those included in the Hageman factor activator. Suitably deionized water is used in the preparation of the solution, and any adjustment of the pH is effected by an organic buffer system formed by the hydroxy alkyl amine and its hydrochloride, that is, any necessary pH change is achieved by addition of the amine or hydrochloric acid.

The lower hydroalkyl amine which is contained in the coating solution has to be water soluble and protein-compatible, in particular, it must not have any precipitating activity towards proteins or otherwise interfere with immunological reactions.

The primary or secondary lower hydroxy alkyl amine suitably is a monoamine containing 2 to 10 carbon atoms and 1 to 3 hydroxy groups which are separated from the amino group by at least 2 carbon atoms.

A preferred group of hydroxy (lower) alkylmonoamines includes primary amines of the formula

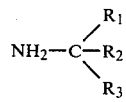

wherein $R_1$ represents hydroxy alkyl containing 1 or 2 carbon atoms, $R_2$ represents hydroxy alkyl containing 1 or 2 carbon atoms, hydrogen or alkyl containing 1 or 2 carbon atoms, and $R_3$ represents hydroxy alkyl containing 1 or 2 carbon atoms, hydrogen or alkyl containing 1 or 2 carbon atoms. Tris (hydroxymethyl)aminomethane is particularly preferred.

Suitably the lower hydroxy alkyl amine is contained in the coating solution in an amount of from about 0.035 to about 0.05 mol/l, preferably in an amount of from about 0.04 to about 0.045 mol/l. For example, tris (hydroxymethyl)aminomethane is suitably used in an amount of from about 4.5 to about 6.5 g/l, preferably in an amount of from about 5.0 to about 5.5 g/l.

The amount of immunologically active agent in the coating solution can vary within the range of from about 0.05 to about 20 g/l, preferably from about 0.5 to about 2 g/l; that is, the coating solution provides a dilution of the immunologically active agent of from about 1 g/50 ml to about 1 g/20,000 ml, preferably from about 1 g/50 ml to about 1 g/2,000 ml. The suitable dilution for a given immunological agent will, of course, depend on the sensitivity of the respective immunological reaction. Furthermore, since most of the immunologically active agents are not pure chemical substances, the activity of a given immunologically active agent may further vary to a certain degree from charge to charge. The activity of a given immunologically active agent is defined by its titer. The titer of an immunologically active agent is defined as the highest dilution in g/ml which yields the optimum immunological response in the given immunological reaction. Determination of the titer of a new charge of a given immunologically active agent by comparison with a standard sample of known activity is common routine in all immunological test procedures. Preferably, the dilution of the immunologically active agent in the coating solution is between about 1 and about 25 times, most preferably about 10 times, higher than its titer, that is, the concentration of the immunologically active agent in the coating solution most preferably is about 10% of the titer concentration.

The coating solution according to the present invention further comprises an amount of from about 0.5 to about 10 g/l of a platelet substitute or a mixture of a platelet substitute and a catalytic amount of a Hageman factor activator.

Platelets are a certain type of blood cells which play a major role in blood coagulation. Platelets release a platelet factor which reacts with several coagulation factors in the blood serum including the so-called Hageman factor to initiate the complicated blood coagulation reaction. In clinical test methods for screening blood plasma and diagnosing disturbances and disorders in blood coagulation, a platelet substitute is commonly used instead of a difficult-to-standardize platelet suspension as a reagent for initiating the coagulation process.

Platelet substitutes are well known in the art and are commercially available. They are brain extracts, usually in lyophilized form, in particular, extracts from rabbit brains containing rabbit brain phospholipids, e.g., rabbit brain cephalin, which is extracted from dehydrated rabbit brains. Procedures for preparing a brain extract which is a platelet substitute by extracting warm blooded mammalian brain tissue are reported by W. N. Bell and H. G. Alton in Nature, 174 880 (1954), and in U.S. Pat. No. 3,395,210. Examples of commercial platelet substitutes are Cephaloplastin ® (manufacturer Dade), Platelin ® (manufacturer Warner-Chilcott) and Thrombolax ® (manufacturer Ortho).

Hageman factor activators are well known in the art. It is further known that the coagulation reaction in clinical tests is accelerated when the platelet substitute is activated by addition of a catalytic amount of a Hageman-factor activator. A Hageman-factor activator may be a physical or a chemical activator. Physical activators include finely divided diatomaceous earth (that is essentially porous silica), bentonite, kaolin celite and powdered glass having a particle size of between about 2 and about 20 microns, and nonporous fumed silica having a particle size of about 20 to about 60 millimicrons, the latter being preferred. The physical activator suitably is contained in the mixture in an amount of from about 0.05 to about 1.0, preferably from about 0.1 to about 0.5% by weight relative to the weight of the brain extract. Chemical activators include hydroxyphenyl compounds and their salts in particular polycyclic compounds containing two mono- or di-hydroxy substituted benzene nuclei, such as hydroxy substituted anthraquinones, e.g. alizarin, and in particular, alkali and ammonium salts of ellagic acid. The chemical activators are suitably present in the mixture in a molar concentration of between about $10^{-8}$ and about $10^{-4}$.

Examples of physical activators and of mixtures of platelet substitutes with physical activators are disclosed in U.S. Pat. Nos. 3,395,210 and 3,880,714.

Examples of chemical activators are disclosed in U.S. Pat. No. 3,486,981. Activated platelet substitutes which contain a chemical or physical activator also are commercially available.

The coating solution is allowed to stay in contact with the organic polymer surface, e.g., is kept in a polymeric test tube, the inner surface of which is to be coated, for a sufficient period of time to allow an immunologically effective amount of the immunologically active agent to be attached thereto. The optimum coating period may vary depending on the affinity of the immunologically active agent to the polymer surface, and the amount of immunologically active agent which, in turn, is dependent on the sensitivity of the immunological reaction in question, as well as on the coating temperature. Suitably, the coating period is from about 15 minutes to about 24 hours, preferably from about 15 minutes to about 5 hours, in particular, from about 30 minutes to about 3 hours. The coating suitably takes place at room temperature or at slightly elevated temperatures, e.g., temperatures up to 50° or 40° C., in particular, 37° C. Subsequently the coating solution is removed, suitably by aspiration with a siphon, and the coated solid phase, e.g., the test tube, is allowed to dry. It is advisable to wash the coated surface once with an aqueous washing solution. Preferably, the washing solution is a buffered isotonic solution, e.g., a 0.9% NaCl solution, containing about 0.1% of gelatin. The lower hydroxy alkyl amine which is contained in the coating solution or a phosphate buffer may be used, suitably in about 0.1 molar concentration.

Suitably the solid phase, e.g., the test tubes, are allowed to dry at room temperature for several hours, e.g., between about 15 hours and 50 hours. In the case where the solid phase is in the form of polymer particles which, suspended in water, form a latex, the amount of solid phase which is brought into contact with the coating solution, that is the amount of polymer latex, is preferably adjusted such that the entire amount of immunologically active agent in the coating solution is adsorbed onto the surface of the polymer particles. No subsequent washing or drying of the solid phase is needed in this event and after the coating period the polymer latex/coating solution mixture as such can be used as a suspension of the coated solid phase.

The resulting immunologically active coated solid phases, e.g., the coated test tubes, are storage-stable for several months without loss or change of their immunological activity.

In case the organic polymer surface is a water wettable matrix of a hydrophyllic gel-forming polymer coated onto the inner surface of a test tube, the platelet substitute and/or the lower hydroxyalkylamine may be omitted from the coating solution. Immunologically active agents which are sufficiently diffusible into a polymer matrix and can be applied to a test tube which is provided with an inner coating of a hydrophyllic polymer matrix in form of a simplified coating solution containing only the immunologically active agent and a buffering amount of the hydroxyalkylamine, include $\beta$-lactoglobulin, intrinsic factor and many enzymes.

As mentioned above, in case the immunologically active agent is sufficiently heat-stable an appropriate amount thereof may be introduced directly into the warm colloid solution of the hydrophyllic polymer (with or without the addition of a lower hydroxyalkylamine and/or a platelet substitute) and thus be applied to the inner surface of the test tube, together with, and embedded into the polymer matrix.

Sufficiently heat-stable immunologically active agents which can be coated in this manner include hepatitis antibody, virus antibodies and antibodies against haptan-protein complexes of drugs, e.g., digoxin antibody. The coating period comprises suitably between about 15 seconds and 2 minutes at a temperature of between 30 and 50, preferably between 35° and 40° C.

The immunologically active coated solid phase of the present invention, e.g., test tubes, a portion of the internal surface of which is coated with the immunlogically active agent, can be used in conventional solid phase immuno assay procedures, and are especially useful for solid phase RIA.

A solid phase RIA technique using a coated solid phase, e.g., a coated tube according to the present invention, comprises contacting an aqueous solution containing a sample of the test liquid wherein a certain immunologically active component, e.g., an antigen, is to be determined, a known amount of radioactive labeled form of said immunologically active component and, optionally, a suitable diluent, e.g. a buffered saline solution, with the coated solid phase, e.g., introducing it into the coated test tube, at least a portion of the surface of which is coated with an immunologically active specific anti-agent for said immunologically active component, e.g., the specific antibody. The dilution of the test liquid in the aqueous solution is chosen such that the total content of unlabeled and labeled immunologically active component is such that a fraction, preferably of from about 50 to about 80% thereof is bonded in the immunological reaction. The incubation suitably takes place at a temperature of between about 4 and about 37° C., preferably at about room temperature. After allowing a sufficient incubation time for the immunological reaction to take place, e.g., a period of between about 1 and about 25 hours, the solution is separated from the solid phase, optionally the latter is washed, e.g., with water or a buffered saline solution, and the radioactive count in the solid support or in the solution is determined. The radioactivity determinations can be effected by conventional methods, e.g., by means of scintillation detectors. Instead of being labeled with a radioactive isotope, the labeled form of the immunologically active component may also be labeled with a fluorescent group. Labeling of the immunologically active material can be done in a conventional manner with a suitable isotope, e.g., $I^{125}$, $C^{14}$ or $H^3$. Radioactive labeled immunologically active agents which are commonly used in clinical testing are commercially available.

The solid phase according to the present invention can be used for qualitative and for quantitative determination.

According to another embodiment of the present invention, the immunologically active solid coated phase is in the form of polymer particles which are suspendable in an aqueous reaction medium. If an immunologically active component, which is responsive to the immunologically active agent in the solid phase is present in the reaction medium, agglutination of the solid phase particles will occur, and can be determined visually microscopically or nephlometrically.

As is common in clinical immuno assay test procedures, a comparative delltermination on a control sample containing a known amount of the immunologically active compound to be determined in an unknown test sample suitably is carried out simultaneously with the determination in the unknown sample. For quantitative analysis the results are interpreted by comparison with a standard curve which is prepared using a series of standard samples containing known varying amounts of the respective immunologically active component.

According to the present invention, there is further provided a means for immuno assays in form of a diagnostic test pack which comprises a first container containing an immunologically active coated solid phase, preferably in the form of a test tube, a portion of the internal surface of which is coated with a first immunologically active agent or a latex of polymer particles, the surface of which is coated with the first immunologically active agent; a second container which comprises a second immunologically active agent which is capable of an immunological binding reaction with said first immunologically active agent; and a third container which comprises a labeled form of said second immunologically active agent or an agent which is capable of reacting with said second immunologically active agent.

The following examples are intended to further describe the invention without limiting it.

EXAMPLE 1

PREPARATION OF DIGOXIN-ANTIBODY COATED TEST TUBES (a) Preparation of the Coating Solution 0.5349 g of tris(hydroxymethyl)aminomethane were dissolved in 50 ml of deionized water by magnetic stirring for about 20 minutes. The pH of this solution was adjusted to about 9.2 by adding 0.1 N of hydrochloric acid. Subsequently, 0.033 ml of a solution of activated platelet substitute* in deionized water were added under stirring and stirring was continued for an additional 10 minutes. 0.03 ml of digoxin antiserum was added under stirring, sufficient deionized water was added to bring the total volume of the coating solution up to 100 ml and stirring was continued for 5 to 10 minutes.

*Commercial product activated Platelin ® manufacturer: General Diagnostics, N.J.; composition: mixture of phopholipids extracted from rabbit brain and micronized silica. The aqueous solution thereof contains 0.3 g/ml of rabbit brain extract and 0.2 mg/ml of micronized silica.

(b) Coating of the Test Tubes

Portions of 1 ml each of the coating solution were dispensed into 12×75 mm polystyrene test tubes and were retained therein for an incubation period of 30 minutes at a temperature of 37° C. Subsequently, the coating solution was removed from the test tubes by siphoning and the tubes were washed once with a washing solution (prepared by dissolving 0.1 mole of tris (hydroxymethyl)amino methane hydrochloride (or alternatively 0.1 mole of sodium phosphate buffer) in aqueous 0.9% NaCl solution containing 0.1% of gelatin. The coated test tubes were dried at room temperature for a period of 18 hours.

*Rinsing with water up to 20 times does not diminish the activity of the tube.

The resulting coating could be washed off by rinsing with aqueous 0.1 NHCl or 0.1 N NaOH.

EXAMPLE 1a

The procedure of Example 1 was repeated using instead of polystyrene test tubes test tubes made of polypropylene.

EXAMPLE 1b

The procedure of Example 1 was repeated using instead of the solution of activated Platelin, a solution of Platelin containing only the rabbit brain extract but no micronized silica.

EXAMPLE 1c

The procedure of Example 1 was repeated using as the solution of activated platelet substitute the commercial product activated cephaloplastin ® manufacturer Dade, composition: rabbit brain extracted cephalin in $10^{-4}$ molar ellagic acid.

EXAMPLE 2

PREPARATION OF DIGOXIN-ANTIBODY COATED TEST TUBES (a) Pretreatment of the Tubes 0.1 ml of glutaraldehyde were dissolved in 100 ml of deionized water. 4.0 ml each of this solution were poured into 12×75 mm polystyrene test tubes. The tubes were heated to a temperature of 60° C. for two hours subsequently the glutaraldehyde solution was poured off and the tubes were each washed two times with 4.0 ml of distilled water, drained and dried at room temperature in inverted position for 18 hours.

The pretreated test tubes were subsequently coated with the coating solution described in Example 1a in the manner described in Example 1b.

The resulting coating could not be washed off by rinsing the tubes with aqueous 0.1 N HCl or 0.1 N NaOH suggesting that the bonding was at least partially provided by covalent linkages.

EXAMPLE 3

PREPARATION OF INTRINSIC FACTOR COATED TEST TUBES (a) Coating of Tubes with Polymer Matrix 1.0 g of agar purified grade (manufacturer Difco) were dissolved in 100 ml of deionized water under stirring at boiling temperature until a clear, transparent and homogenus solution was obtained. The agar solution was allowed to cool at about 50° C. Portions of 1.0 ml each of the hot agar solution are dispensed into 12×75 mm polystyrene or glass test tubes which are kept at a temperature of 37° C. in a water bath. After a period of 30 to 60 seconds, the agar solution is aspirated from the test tubes and the test tubes are dried at room temperature.

(b) Coating of the Matrix Coated Tubes with Intrinsic Factor 62.5 mg of intrinsic factor are dissolved in 20 ml of deionized water. This solution then is further diluted with deionized water to obtain a final concentration of 60 nanogram/ml of the intrinsic factor.

Portions of 1.0 ml each of the solution are dispensed into the dried matrix coated test tubes and kept therein at room temperature for a period of 1 to 2 hours. Subsequently the solution is carefully aspirated and decanted and the tubes are allowed to dry at room temperature for a period of about 24 hours.

EXAMPLE 4

PREPARATION OF DIGOXIN ANTIBODY COATED TEST TUBES

An agar solution was prepared and cooled to about 50° C. as described in Example 4a. A solution of 0.03 ml of digoxin antiserum in 100 ml of water was added to the hot agar solution and mixed by stirring in about 10 minutes. 12×75 mm polystyrene or glass tubes were coated with the hot digoxin antiserum-containing agar solution in the manner described in Example 3.

EXAMPLE 5

PREPARATION OF HCG COATED POLYSTYRENE PARTICLE SUSPENSION (LATEX)

10 ml of 10% suspension of polystyrene particles having a particle size of between about 1.2 and 1.5 microns are added to 100 ml of a coating solution which is prepared as described in Example 1 but using 10 mg of HCG instead of the digoxin antiserum.

In resulting latex all of the HCG has been absorbed into the polystyrene particles. The pH of the resulting dilute of coated polystyrene latex may be adjusted to the optimum pH for the immunological reaction between HCG and anti-HCG-serum that is to about 7.6.

EXAMPLE 5a

The procedure of Example 5 was repeated using instead of the polystyrene suspension a suspension of polypropylene particles in deionized water.

EXAMPLES 6 TO 16

The following immunologically active coated polystyrene test tubes or polystyrene latexes were prepared according to the procedures described in Examples 1 to 5 under the condition given in Table I below.

TABLE I

| Ex No | Immunolog. Act. Agent | Dilution v/v of immunolog. Act. Agent in Coating Solution | Coating Method of Ex | Coating Time | Coating Temperature |
|---|---|---|---|---|---|
| 6 (Latex) | Thyroxin | 10 mg/100 ml | 5 | 30 min 18 h | 37° C. −4° C. |
| 7 (Latex) | Rheumatoid Arthritis Antiserum | 1:100 | 5 | 30 min 18 h | 37° C. 4° C. |
| 8 (Tube) | Anti-Thyroxin Antiserum | 1:500 | 1 | 2 h | 37° C. |
| 9 (Tube) | Antiestriol Antiserum | 1:500 | 2 | 30 min | 37° C. |
| 10 (Tube) | Anti-Iniodothyronine Antiserum | 1:1000 | 1 | 2 h | 37° C. |
| 11 (Tube) | Anti-TSH Antiserum | 1:1000 | 2 | 18–24 | 37° C. |
| 12 (Tube) | Toubramycin Antiserum | 1:1000 | 1 | 30–60 min | 37° C. |
| 13 (Tube) | Gentamycin Antiserum | 1:1000 | 1 | 30–60 min | 37° C. |
| 14 | Anti-Hepatitis-B Antiserum | 1:2000 | 1 | 3 h | 45° C. |
| 15 | Anti-Cortisol Antiserum | 1:500 | 1 | 2 h | 37° C. |
| 16 | B-Lacto Globulin | 50 μg/ml | 3 | 3h | Room Temperature |

EXAMPLE 17

Influence of coating conditions and incubation on immunological binding activity of diogoxin antibody coated polystyrene tubes.

The test tubes were coated according to the procedure described in Example 1 or 2 under the conditions given in Table II below.*

*The resulting coatings were highly uniform: coefficient of variation in 50 handcoated tubes between 2.3 and 3.2% stability of coating at 63° C.: >1 month.

The immunological binding activity of the coated tubes was determined by introducing 1 ml of a tracer solution containing an amount of $I^{125}$ labeled digoxin in phosphate buffered saline (0.9% NaCl) solution having a radioactivity of 0.01 micro curi/ml. After incubation under the conditions given in Table II below the tracer solution was aspirated, the tube was washed twice with water, the tube is counted for 1 minute in a gamma counter. Based on the radioactive count, the % binding of the radioactively labeled diogoxin antigen is calculated. The results are given in Table II below.

(a) Anti-thyroxin antibody coated test tubes of Example 8

TABLE II

ACTIVITY OF DIGOXIM ANTIBODY COATED TUBES

| Test No. | Procedure of Example | Dilution of Antibody in Coating Solution | pH of Coating Solution | Coating Time | Coating Temperature | Incubation Temperature | Incubation Time | % Binding |
|---|---|---|---|---|---|---|---|---|
| 17a | 1 | 1:1000 | 9.0 | 30' | 37° C. | 37° C. | 45' | 49.6 |
| 17b | 1 | 1:2000 | 9.0 | 30' | 37° C. | 37° C. | 45' | 53.06 |
| 17c | 1 | 1:4000 | 9.0 | 30' | 37° C. | 37° C. | 45' | 53.6 |
| 17d | 1 | 1:8000 | 9.0 | 30' | 37° C. | 37° C. | 45' | 50.7 |
| 17e | 1 | 1:16000 | 9.0 | 30' | 37° C. | 37° C. | 45' | 45.9 |
| 17f | 1 | 1:3000 | 8.87 | 30' | 37° C. | 37° C. | 45' | 34.0 |
| 17g | 1 | 1:3000 | 9.0 | 30' | 37° C. | 37° C. | 45' | 35.3 |
| 17h | 1 | 1:3000 | 9.4 | 30' | 37° C. | 37° C. | 45' | 51.16 |
| 17i | 1 | 1:3000 | 10.37 | 30' | 37° C. | 37° C. | 45' | 54.9 |
| 17j | 1 | 1:3000 | 10.37 | 15' | 37° C. | 37° C. | 45' | 52.0 |
| 17k | 1 | 1:3000 | 10.37 | 45' | 37° C. | 37° C. | 45' | 54.66 |
| 17l | 1 | 1:3000 | 10.37 | 120' | 37° C. | 37° C. | 45' | 59.7 |
| 17m | 2 | 1:1000 | 9.0 | 30' | 37° C. | 37° C. | 45' | 44.96 |
| 17n | 2 | 1:200 | 9.0 | 30' | 37° C. | 37° C. | 45' | 57.68 |
| 17o | 2 | 1:4000 | 9.0 | 30' | 37° C. | 37° C. | 45' | 56.68 |
| 17p | 2 | 1:8000 | 9.0 | 30' | 37° C. | 37° C. | 45' | 52.5 |

EXAMPLE 18

DETERMINATION OF DIGOXIN LEVEL IN SERUM BY SOLID PHASE RIA USING DIGOXIN-ANTIBODY COATED TUBES (A) Reagents:
(a) Anti-digoxin antibody coated tubes prepared as described in Example 1
(b) digoxin standard solutions containing 0.5, 1.0, 2.0, 4.0, and 6.0 ng/ml respectively of digoxin dissolved in serum
(c) a serum blank
(d) tracer solution containing $I^{125}$ digoxigenin in a concentration corresponding to 1.0 micro curie ($\mu$Ci)/5 ml in a tris(hydroxymethyl) amino methane/HCl buffered saline (0.9% NaCl) solution having a pH of 7.4

(B) Preparing of standard curve:
50 $\mu$l samples of the digoxin standard solutions and the serum blank each are introduced into an antibody-coated test tube, 1 ml of the tracer solution is added to each tube, the tubes are incubated at a temperature of 37° C. for a period of ½ hour. Subsequently the contents of the tubes are washed once with 5.0 ml of distilled water, drained dried and counted for 1 minute. A standard curve is prepared by plotting the number of counts per minutes (cpm) against the digoxin concentration in the standard solution.

(C) Determination of digoxin level in patient's serum A 50 $\mu$l sample of the patient's serum is treated as described in (B) and the digoxin level therein is determined by comparing the (cpm) of the coated tube with the standard curve.

EXAMPLE 19

DETERMINATION OF THYROXIN LEVEL IN SERUM BY SOLID PHASE RIA USING THYROXIN ANTIBODY COATED TUBES

The thyroxin level in serum is determined by the method as described in Example 18, using the following reagents and incubation conditions:
(A) Reagents (b) thyroxin standard solutions centering 1, 4, 12, 18 and 30 $\mu$g/ml respectively of thyroxin dissolved in serum
(c) a tracer solution containing 125 I labeled thyroxin in a concentration corresponding to 1.0 $\mu$Ci/5 ml in a tris(hydroxymethyl) amino methane/HCl buffered saline solution having a pH of about 7.4
(c) a serum blank (B) Incubation Conditions
Volume of serum samples 25 $\mu$l
Incubation Time: 90 minutes
Incubation Temperature: Room Temperature

EXAMPLE 20

DETERMINATION OF TSH LEVEL IN SERUM BY SOLID PHASE RIA USING TSH ANTIBODY COATED TUBES

The TSH level in serum is determined by the method as described in Example 18, using the following reagents and incubation conditions:
(A) Reagents
(a) Anti TSH antibody coated test tubes of Example 11
(b) TSH standard solutions containing 2.5, 5, 10, 20 and 40 $\mu$IU/ml respectively of TSH dissolved in serum
(d) a serum blank
(c) a tracer solution containing 125 I labeled TSH in a concentration corresponding to 1.0 $\mu$Ci/5 ml in a phosphate buffered saline solution.

(B) Incubation Conditions
Volume of serum samples: 50 ug
Incubation Time: 3 hours
Incubation Temperature: 37° C.

EXAMPLE 21

DETERMINATION OF ESTRIOL LEVEL IN SERUM BY SOLID PHASE RIA USING ESTRIOL ANTIBODY COATED TUBES

The estriol level in serum is determined by the method as described in Example 18, using the following reagents and incubation conditions:
(A) Reagents (a) Anti-estriol antibody coated test tubes of Example 8
(b) estriol standard solutions containing 1, 5, 10, 12, 40 and 80 ng/ml respectively of estriol dissolves in serum
(c) a serum blank
(d) a tracer solution containing 125 I labeled estriol in a concentration corresponding to 1.0 μCi/5 ml in a tris(hydroxymethyl) amino methane/HCl buffered saline solution having a pH of about 7.4.
(B) Incubation Conditions
Volume of serum samples: 25 μg
Incubation Time: 90 minutes
Incubation Temperature: room temperature

EXAMPLE 22

DETERMINATION OF VITAMIN B12 LEVEL IN SERUM BY SOLID PHASE RIA USING INTRINSIC FACTOR COATED TUBES

The vitamin B12 level in serum is determined by the method as described in Example 18, using the following reagents and incubation conditions:
(A) Reagents
(a) Coated test tubes of Example 3
(b) Vitamin B12 standard solutions containing 50, 100, 300, 600, 1200 and 1800 pcg/ml respectively of vitamin B12 dissolved in serum
(c) a serum blank
(d) a tracer solution containing 57Co-labeled vitamin B12 in a concentration corresponding 1.0 μCi/5 ml in saline
(B) Incubation Conditions:
Volume of serum samples: 50 μl
Incubation Time: 1 hour
Incubation Temperature: Room temperature

EXAMPLE 23

Detection of HCG in Serum Using the HCG Coated Polystyrene Latex of Example 5

On a blackened slide there are placed a 50 μl sample of a patient's serum to be tested, 50 μl of a 1:400 dilution of anti-HCG-serum in phosphate buffered saline (0.9% Na Cl) solution, and 50 μl of the HCG coated polystyrene latex of Example 5 and mixed using a wooden applicator stick. The slide is rotated for two minutes and then is visually examined for agglutination.

Two control tests are carried out using instead of the patient's serum sample to be tested 50 μl of negative control serum, that is a serum blank, or respectively 50 μl of a positive control serum containing 1–2 international units of HCG per ml.

Macroagglutination between the HCG coated latex and the anti-HCG-serum is seen in the negative control test. No agglutination takes place in the positive control test where the anti-HCG-serum is neutralized by the HCG in the positive control serum.

Thus, if no agglutination takes place in test with the patient's serum, this shows the presence of HCG.

EXAMPLE 24

Determination of Hepatitis B Antigen in Serum by Solid Phase RiA

A. Reagents:
1. anti-hepatitis B antiserum coated test tubes prepared according to Example 14
2. Positive control serum containing 2 ng/ml of hepatitis B antigen
3. negative control serum (serum blank)
4. tracer consisting of $I^{125}$ labeled anti-hepatitis B antiserum (guinea pig)

B. Procedure

Introduce a 50 μl sample of the patient's serum to be tested, of the negative control serum and of the positive control serum, respectively, each into an antibody coated tube.
Incubate for 2 hours at 45° C.
Wash 3 times with distilled water.
Add 100 μl of $I^{125}$ hepatitis B antiserum.
Incubate at 45° C. for 1 hour.
Wash 3 times with distilled water
Count the tubes.

Compare cpm of the tube with patient's serum with those with negative control serum and positive control serum for determining if the unknown patient's sample contains hepatitis B antigen. test kits according to the present invention are given A. Pregnancy test kit containing:
1. a first container containing the HCG coated polystyrene latex of Example 5
2. a second container containing a 1:400 dilution of anti HCG serum in phosphate buffered saline solution
3. a third container containing a serum blank (negative control serum)
4. a fourth container containing a serum containing 1–2 international units of HCG/ml (positive control serum)
5. a blackened glass slide B. Digoxin level test kit containing:
1. digoxin-antibody coated polystyrene test tubes
2. a plurality of containers containing standard solution containing 0, 0.5, 1.0, 2.0, 4.0 and 6.0 ng/ml respectively of digoxin in serum
3. a container containing a tracer solution containing an amount of $I^{125}$ digoxigenin in a concentration corresponding to 1.0 u Ci/5 ml in a tris(hydroxymethyl) amino methane/H Cl buffered saline (0.9% Na Cl) solution having a pH of 7.4.

C. Hepatitis antigen test containing:
1. anti-hepatitis B antibody coated polystyrene test tubes of Example 14
2. a first container containing $I^{125}$-labeled hepatitis B antiserum (guinea pig)
3. a second container containing a serum blank (negative control serum)
4. a third container containing a serum containing 2 ng/ml of hepatitis B-antigen (positive control serum)

D. Thyroxin level test kit containing:
1. thyroxin-antibody coated polystyrene test tubes of Example 8
2. a plurality of containers containing standard solution containing 0, 1, 4, 8, 12, 20 and 30 μg respectively of thyroxin in 100 ml of serum each
3. a container containing a tracer solution containing an amount of $I^{125}$ thyroxin in a concentration corresponding to 1.0 μCi/5 ml in a tris (hydroxymethyl) amino methane/H Cl buffered saline (0.9% Na Cl) solution having a pH of 7.4.

E. Estriol level test kit containing:
1. estriol-antibody coated polystyrene test tubes of Example 9

2. a plurality of containers containing standard solution containing 0, 2.5, 5, 10, 20, 40 and 80 ng/ml respectively of estriol in human serum
3. a container containing a tracer solution containing an amount of $I^{125}$ estriol in a concentration corresponding to 1.0 μCi/5 ml in a phosphate buffered saline (0.9% Na Cl) solution
4. a container containing 0.9% Na Cl solution containing 0.1 mol/l of phosphate buffer F. Cortisol level test kit containing:
  1. cortisol-antibody coated polystyrene test tubes of Example 15
  2. a plurality of containers containing standard solution containing 0, 1, 4, 8, 16, 32 and 64 μg respectively of cortisol in 100 ml of serum
  3. a container containing a tracer solution containing an amount of $I^{125}$ cortisol in a concentration corresponding to 1.0 μCi/5 ml in a phosphate buffered saline (0.9% Na Cl) solution
  4. a container containing 0.9% Na Cl solution containing 0.1 mol/l of phosphate buffer G. Toubromycin level test kit containing:
  1. toubromycin-antibody coated polystyrene test tubes of Example 12
  2. a plurality of containers containing standard solution containing 0, 2, 4, 8, 16 and 30 μg respectively of digoxin in 100 ml of serum
  3. a container containing a tracer solution containing an amount of $I^{125}$ toubromycin in a concentration corresponding to 1.0 μCi/5 ml in phosphate buffered saline (0.9% Na Cl) solution
  4. a container containing 0.9% Na Cl solution containing 0.1 mol/l of phosphate buffer H. Gentamycin level test kit containing
  1. gentamycin-antibody coated polystyrene test tubes of Example 13
  2. a plurality of containers containing standard solution containing 0, 2, 4, 8, 16 and 30 μg respectively of gentamycin in 100 ml serum
  3. a container containing a tracer solution containing an amount of $I^{125}$ gentamycin in a concentration corresponding to 1.0 μCi/5 ml in a phosphate buffered saline (0.9% Na Cl) solution
  4. a container containing 0.9% Na Cl solution containing 0.1 mol/l of phosphate buffer

What is claimed is:

1. A method for preparing an immunologically active coated solid phase by coating the surface of a solid support material having an organic polymer surface with an immunologically active agent which comprises the steps of:
  (a) contacting the organic polymer surface of the solid support material with an aqueous coating solution having a pH-value of from about 8.5 to about 10.5 and comprising dissolved therein an amount of from about 0.035 to about 0.05 mol/l of a water soluble protein-compatible primary or secondary hydroxy lower alkyl amine, an amount of between 0.05 and about 20 g/l of a water/soluble immunologically active agent and an amount of from about 0.05 to about 10 g/l of a blood platelet substitute which is a brain extract containing phospholipids and cephalin for a sufficient period of time to allow an immunologically effective amount of the immunologically active agent to be attached to the organic polymer surface of the solid support material to obtain an immunologically active coating therein,
  (b) removing the coating solution from the coated solid support material
  (c) allowing the coated solid support material to dry.

2. The method as defined in claim 1 wherein the immunologically active agent has a molecular weight of at least 20000 and the solid support material is a water insoluble solid organic polymer.

3. The method as defined in claim 2 wherein the immunologically active agent has a molecular weight of between about 50000 and about 200000.

4. The method as defined in claim 2 wherein the immunologically active agent has a molecular weight of between about 20000 and about 200000 and which further comprises the step of pretreating the surface of the solid organic prepolymer with an aqueous solution of a water soluble dialdehyde containing 3 to 8 carbon atoms.

5. The method as defined in claim 1 wherein the immunologically active agent has a molecular weight of between about 5000 and about 200000 and the organic polymer surface of the support material is a polymer matrix which is a film coating of a protein-compatible hydrophylic gel forming polymer.

6. The method as defined in claim 1 wherein the platelet substituted further comprises a catalytic amount of a Hageman-factor activator.

7. A method for determining immunologically active components in an aqueous liquid which comprises the steps of
  (a) contacting an immunologically active coated phase at least a portion of the surface of which is coated with an immunologically active anti-agent for said immunologically active component by the method as defined in claim 1 with an aqueous solution comprising a sample of said liquid and a known amount of a labeled form of said immunologically active component for a sufficient period of time for an immunological binding reaction to take place whereby portions of the labeled and unlabeled immunologically active component are bound onto the immunologically active solid phase
  (b) separating said solution from said solid phase and
  (c) determining the amount of a labeled component in the solid phase or in the solution.

8. A method for detecting an immunologically active agent in an aqueous liquid which comprises the steps of
  (a) contacting a suspendable particulate immunologically active coated phase, the surface of which is coated with the immunologically active agent by the method as defined in claim 1 with an aqueous solution comprising a sample of said liquid and a known amount of an immunologically active anti-agent for said immunologically active agent for a sufficient period of time for an immunological binding reaction to take place,
  (b) determining the amount of agglutination between the particulate immunologically active phase and the immunologically active anti-agent.

9. A means for carrying out solid phase immuno assays which is in the form of a package which comprises a first container containing an immunologically active coated solid phase, the surface of which is coated with a first immunologically active agent by the method as defined in claim 1;
  a second container which comprises a second immunologically active agent which is capable of an immunological binding reaction with said first immunologically active agent; and
  a third container which comprises a labeled form of said second immunologically active agent or an agent which is capable of reacting with said second immunologically active agent.

* * * * *